United States Patent [19]

Agback

[11] 4,045,429
[45] Aug. 30, 1977

[54] 4-(4-HYDROXY- OR ACETOXY-3-CARBOMETHOXY-PHENYLAZO)-BENZENESULPHONYL CHLORIDE

[75] Inventor: Karl Hubert Agback, Uppsala, Sweden

[73] Assignee: Pharmacia Aktiebolag, Rapsgatan, Sweden

[21] Appl. No.: 571,653

[22] Filed: Apr. 25, 1975

Related U.S. Application Data

[63] Continuation of Ser. No. 119,834, March 1, 1971, abandoned.

[30] Foreign Application Priority Data

Mar. 6, 1970 Sweden ............................. 2987/70

[51] Int. Cl.$^2$ ................. C07C 107/04; C07C 107/06
[52] U.S. Cl. ................................. 260/207; 260/156; 260/207.1; 424/226
[58] Field of Search ............... 260/156, 207, 207.1, 260/543 R; 424/226

[56] References Cited

U.S. PATENT DOCUMENTS

| | | | |
|---|---|---|---|
| 2,307,650 | 1/1943 | Tisza et al. | 260/156 X |
| 2,396,145 | 3/1946 | Anders et al. | 260/156 |
| 2,426,313 | 8/1947 | Ludwig et al. | 260/156 X |
| 2,482,752 | 9/1949 | Hazleton | 424/226 |
| 2,496,151 | 1/1950 | Dawson et al. | 260/206 |
| 2,658,916 | 11/1953 | Krems | 260/556 |
| 2,816,103 | 12/1957 | Schmid et al. | 260/162 |
| 2,852,557 | 9/1958 | Schraufstatter | 260/519 |
| 2,888,486 | 5/1959 | Gregory | 260/543 R |
| 2,920,072 | 1/1960 | Kolliker et al. | 260/207 |
| 3,055,928 | 9/1962 | Flores et al. | 260/543 R X |
| 3,681,319 | 8/1972 | Lindberg | 260/156 |

FOREIGN PATENT DOCUMENTS

| | | | |
|---|---|---|---|
| 1,499,060 | 9/1967 | France | 260/206 |
| 842,379 | 6/1952 | Germany | 260/146 R |
| 60,059 | 5/1947 | Netherlands | 260/156 |

OTHER PUBLICATIONS

Vargas et al., Chemical Abstracts, vol. 42, 8955 (1948).
Escubos et al., Chemical Abstracts, vol. 43, 3385 (1949).
Goldyrev et al., Chemical Abstracts, vol. 32, 5800–5801 (1938).
Sprysuov et al., Chemical Abstracts, vol. 45, 2434 (1951).

*Primary Examiner*—Floyd D. Higel
*Attorney, Agent, or Firm*—Fred Philpitt

[57] ABSTRACT

A method for the preparation of 2-[4-(4-hydroxy-3-carboxyphenylazo)-benzenesulfonamido]-pyridine by reacting 4-diazobenzenesulfonic acid with an ester of salicyclic acid having the formula

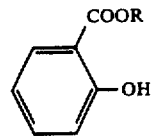

in the presence of an alkali metal hydroxide to form a first reaction product having the formula

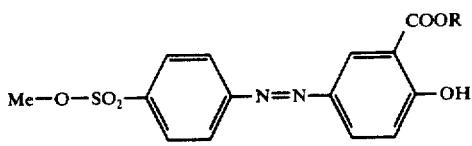

reacting said first reaction product with an acylating agent to form a second reaction product having the formula

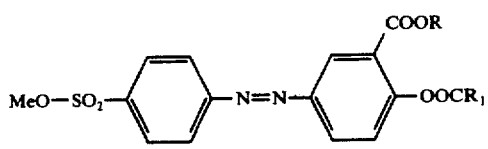

treating said second reaction product with thionyl chloride in the presence of a tertiary formamide to form a chlorinated compound having the formula

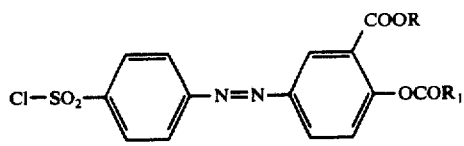

reacting said chlorinated compound with 2-amino-pyridine under water-free conditions in the presence of an acid binding agent, to form a third reaction product having the formula

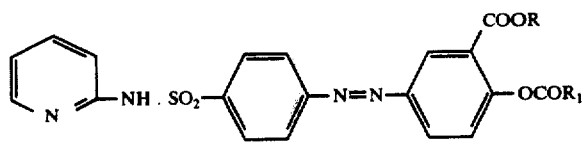

treating said third reaction product with alkali metal hydroxide in the presence of water to hydrolyze off the R and R$_1$ groups, and recovering 2-[4-(4-hydroxy-3-carboxyphenylazo)-benzenesulfonamido]-pyridine.

3 Claims, No Drawings

4-(4-HYDROXY- OR ACETOXY-3-CARBOMETHOXYPHENYLAZO)-BENZENESULPHONYL CHLORIDE

This is a continuation of application Ser. No. 119,834, filed Mar. 1, 1971, now abandoned.

The present invention relates to a new method for the preparation of 2-[4-(4-hydroxy-3-carboxyphenylazo)-benzenesulphonamido]-pyridine (salicylazosulphopyridine) having the formula I

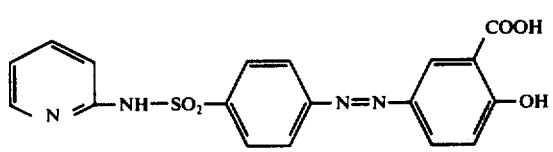

(I)

This compound has an extremely wide therapeutical use and is particularly useful in the treatment of ulcerative colitis.

It has now been found that hitherto unknown intermediates are very well suited for the preparation of the compound disclosed in the introduction above, this compound being obtained directly in a pure form by means of simple reaction steps and in extremely high and reproducable yields by using the new method of the present invention.

In accordance with the method of the present invention 4-diazobenzenesulphonic acid is reacted with an ester of salicylic acid having the formula II

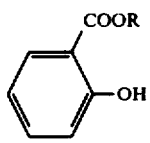

(II)

wherein R represents a lower alkyl group, in alkaline solution, whereafter the product having the formula III

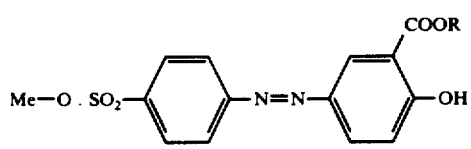

(III)

wherein R has the significance given above and Me represents hydrogen, the equivalent of a metal or an organic salt residue, which is transformed into its acyl derivative by reacting with an acylating agent containing the residue R,CO-, wherein R is a lower alkyl group, to thereby produce a material having the formula IV

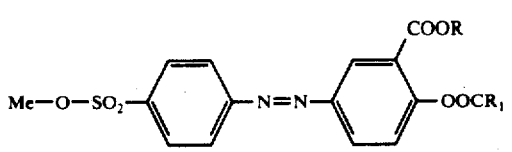

(IV)

wherein R and Me have the same meaning as above and $R_1$ which is a lower alkyl group, is chlorinated, whereafter the product of the formula V

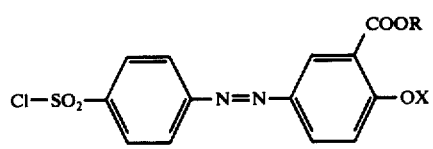

(V)

wherein R has the same meaning as above and X represents hydrogen or the residue $-OCR_1$, wherein $R_1$ has the significance given above, is reacted with 2-aminopyridine in the presence of an acid binding agent to form a compound of the formula VI

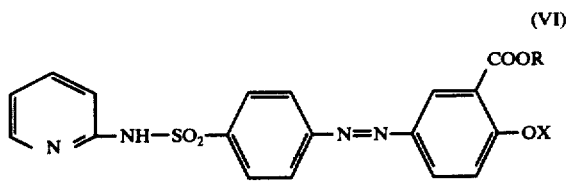

(VI)

wherein R and X have the same meaning as above, which compound is then hydrolysed and the compound of formula I thus obtained is isolated as such or in the form of a physiologically acceptable salt.

The acyl derivative of the formula IV above is obtained by reacting the compound of formula III with an acylating agent containing the residue $R_1CO-$, wherein $R_1$ is a lower alkyl group. As the acylating agent first of all an acid chloride having the formula $R_1CO,Cl$ or an acid anhydride of the formula $R_1CO-O-OCR_1$ is contemplated. When an acid chloride is used, the reaction is carried out in the presence of an acid binding agent. When an anhydride is used, the reaction is preferably effected in the presence of catalytic quantities of mineral acids or organic bases, such as pyridine. The group $R_1CO-$ is preferably acetyl. If the group $R_1CO-$ is acetyl, the hydroxy compound is reacted preferably with acetic acid anhydride, optionally in the presence of acetic acid.

The group Me preferably comprises an alkalimetal equivalent.

The chlorinating agent used for the preparation of the compound of formula V may, for example, be phosphorous pentachloride, phosphorous oxychloride, phosgene and thionyl chloride. It is very suitable to use thionyl chloride in the presence of a tertiary formamide, e.g. dimethyl formamide. The reaction is effected preferably in the presence of an inert organic solvent, e.g. a chlorinated hydrocarbon or a solvent of the benzene series such as benzene, toluene, xylene or chlorobenzene.

The compound of formula VI may optionally be isolated before being hydrolysed. The reaction product, however, is preferably used directly without being isolated prior to the hydrolysing step.

Preferably the compound of formula III is transformed into its acyl derivative of formula IV before the chlorinating step. The coupling between the compound of the formula V and 2-aminopyridine will be facilitated in this way.

Also if X in the formula VI above is a residue of the formula $R_1CO-$ the yields will generally become higher and the compound of formula VI will be purer than in case of X being a hydrogen atom.

The reaction between the sulphonyl chloride and 2-aminopyridine can be carried out in the presence of water, but is preferably effected in a water-free medium in order to avoid hydrolysis of the sulphonyl chloride. In the latter case, the acid binding agent used is preferably an organic tertiary amine such as trimethyl amine or heterocyclic nitrogen-containing compounds such as pyridine. Furthermore, an excess of 2-aminopyridine can be used as the acid binding agent. When pyridine is used as the acid binding agent, the reaction can be effected to advantage with an excess of pyridine as solvent.

The hydrolysis of the intermediate product is preferably effected in a homogeneous solution in water or a polar organic solvent or a mixture thereof. Preferably, an aqueous solution of an alkalimetal hydroxide is used, the product after the hydrolysis being precipitated by the addition of a mineral acid or an orgainc acid such as formic acid or acetic acid. After filtering and careful washing with water, an exceptionally pure salicylazosulphapyridine is obtained, with a yield of approximately 90%. Analyses show that the obtained product fulfills with a good margin the requirements of quality for therapeutical use.

The reactions taking place during the method according to the invention, may, when X is acetyl and R is methyl, be illustrated by the following formulae:

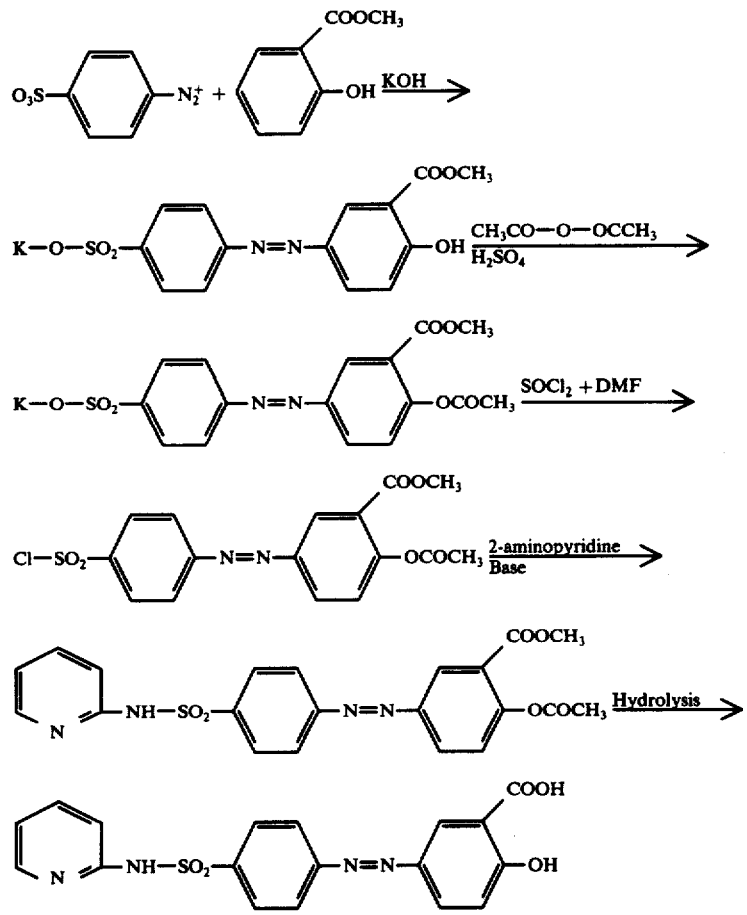

The present invention is further illustrated by the following specific Examples:

EXAMPLE 1

Salicylazosulphapyridine

A solution of 17.3 g of sulphanilic acid, 6.9 g of potassium carbonate and 200 ml of water is cooled to 10° C, and 7.4 g of sodium nitrite in 20 ml of water are added. The solution is poured with rapid stirring into 20 ml of concentrated hydrochloric acid and 125 g of ice and the mixture is allowed to stand for 10 – 15 min at 0° C. A cold solution of 15.2 g of methyl salicylate, 13 g of potassium hydroxide and 100 ml of water is prepared and the diazonium salt mixture is added with rapid stirring. After 5 min the pH is adjusted to 4 and the mixture is heated, whereupon the precipitated azo dye goes into solution. The mixture is cooled and filtered. 33 g of potassium 4-(4-hydroxy-3-carbomethoxy-phenylazo)-benzenesulphonate are obtained, The product, 150 ml of acetic anhydride, 20 ml of acetic acid and 6 drops of sulphuric acid are refluxed until all substances are dissolved. The solution is cooled, 400 ml of ether are added, and the precipitate is filtered off. 33.2 g of potassium 4-(4-acetoxy-3-carbomethoxy-phenylazo)-benzenesulphonate are obtained.

14.1 g of this product are suspended in 33 ml of dimethylformamide. 10 ml of thionyl chloride are added with cooling. After 2 min the solution is poured into cold water. After filtration, washing with water and petroleum ether, the product weighs 11.6 g. The melting point of 4-(4-acetoxy-3-carbomethoxyphenylazo)-benzenesulphonyl chloride is 139° – 140° C after recrystallization.

2.0 g of aminopyridine is dissolved in 8 ml of dry pyridine. 8.0 g of the above product are added in portions with cooling and stirring, holding the temperature below 40° C. The mixture is stirred at ambient temperature for 2 h. 17 ml of 5-normal hydrochloric acid are added with rapid stirring and cooling. The crystals are filtered off and washed with water. The moist intermediate is dissolved in 100 ml of water and 3.4 g of sodium hydroxide and heated to about 70° C for 2 h. The solution is cooled and slowly acidified while stirring rapidly with dilute hydrochloric acid to pH 2 - 3. The crystals are filtered off and washed carefully with water. Salicylazosulphapyridine is obtained in a yield of 7.05 g, corresponding to 88%. The product is light yellow and melts with decomposition above 250° C.

EXAMPLE 2 a.

2-[4-(4-acetoxy-3-carbomethoxy-phenylazo)-benzenesulphonamido]-pyridine 4.0 g of 2-aminopyridine are added to 32 ml of toluene, and about 8 ml toluene are distilled off. The temperature is decreased to 40° - 50° C, and 8.0 g of 4-(4-acetoxy-3-carbomethoxy-phenylazo)-benzenesulphonyl chloride are added with stirring and careful heating so that the temperature is held at 60° - 70° C for 10 - 15 min. The mixture is allowed to come to room temperature. After 1 h the precipitated product is filtered off and carefully washed with water and dried. 8.35 g of the title compound are obtained with melting point 204° - 207° C.

Analysis: Calculated: C, 55.5; H, 4.0; N, 12.3. Found: C, 55.6; H, 3.9; N, 12.3.

b. Salicylazosulphapyridine

The above product is hydrolyzed by heating to 70° - 80° C for 1 h in 100 ml of 0.85-normal sodium hydroxide and acidified with acetic acid, whereupon pure salicylazosulphapyridine is obtained in nearly quantitative yield.

EXAMPLE 3 a.

4-(4-hydroxy-3-carbomethoxy-phenylazo)-benzenesulphonyl chloride 17.6 g of potassium 4-(4-hydroxy-3-carbomethoxy-phenylazo)benzenesulphonate, 30 ml of benzene, 2 ml of dimethylformamid and 6 ml of thionyl chloride are heated to the boiling point under reflux for 30 min. The mixture is cooled, and cold water and 100 ml of petroleum ether are added with rapid stirring. The product is filtered off and washed with water and dried, whereupon 15.4 g of the title compound are obtained. The melting point is 137° - 138° C after recrystallization.

b. Salicylazosulphapyridine 7.1 g of the above chloride are added to 4.0 g of 2-aminopyridine and 24 ml of toluene with careful heating to 40° - 50° C. After the addition the temperature is increased to 70° C, and the mixture is allowed to cool to room temperature. 125 ml of 1-normal sodium hydroxide are added and the mixture is heated until two clear phases are obtained. The toluene phase is removed and the water phase extracted with ether and heated to 100° C for 30 min. After precipitation with acetic acid the title compound is obtained with a melting point of 249° C with decomposition.

What I claim is:
1. The compound having the formula

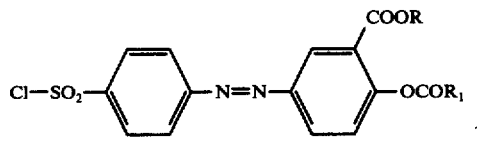

wherein R and R₁ each represent a methyl group.
2. 4-(4-acetoxy-3-carbomethoxy-phenylazo)benzenesulfonyl chloride.
3. 4-(4-hydroxy-3-carbomethoxy-phenylazo)benzenesulfonyl chloride.

* * * * *